United States Patent
Kojic et al.

(10) Patent No.: US 10,159,793 B2
(45) Date of Patent: Dec. 25, 2018

(54) NOZZLE FOR USE IN AN ULTRA-HIGH VELOCITY INJECTION DEVICE

(71) Applicant: Portal Instruments, Inc., Cambridge, MA (US)

(72) Inventors: Nikola Kojic, Winchester, MA (US); Bridget Hunter-Jones, Lincoln, MA (US); Ian W. Hunter, Lincoln, MA (US)

(73) Assignee: Portal Instruments, Inc., Cambridge, MA (US)

( * ) Notice: Subject to any disclaimer, the term of this patent is extended or adjusted under 35 U.S.C. 154(b) by 333 days.

(21) Appl. No.: 14/788,001

(22) Filed: Jun. 30, 2015

(65) Prior Publication Data

US 2015/0374921 A1    Dec. 31, 2015

Related U.S. Application Data

(60) Provisional application No. 62/018,809, filed on Jun. 30, 2014.

(51) Int. Cl.
*A61M 5/30* (2006.01)
*B05B 1/02* (2006.01)

(52) U.S. Cl.
CPC .......... *A61M 5/3007* (2013.01); *A61M 5/30* (2013.01); *B05B 1/02* (2013.01)

(58) Field of Classification Search
CPC .......... A61M 5/30; A61M 5/3007; B05B 1/02
USPC ...................................... 239/601; 604/68, 70
See application file for complete search history.

(56) References Cited

U.S. PATENT DOCUMENTS

| | | | |
|---|---|---|---|
| 7,833,189 B2 | 11/2010 | Hunter et al. | |
| 8,172,790 B2 | 5/2012 | Hunter et al. | |
| 8,328,755 B2 | 12/2012 | Hunter et al. | |
| 2011/0215177 A1* | 9/2011 | Guerrassi | F02M 61/182 239/533.12 |

* cited by examiner

*Primary Examiner* — Darren W Gorman
(74) *Attorney, Agent, or Firm* — Occhiuti & Rohlicek LLP

(57) ABSTRACT

An exemplary embodiment of the invention is a nozzle, for use in an injection device, that projects material at an ultra-high velocity. The nozzle includes an integrally formed body having an interior passageway that has a longitudinal axis. The input of the nozzle is configured to interface with a cartridge, and the output is configured to be placed proximate to a target. The passageway includes a taper, and its path length, from an initial diameter to a position along the passageway where the passageway first reaches a smallest diameter, is at least 0.5 mm. The taper of the passageway defines a shape, in a plane that includes the longitudinal axis, that is a continuous and monotonically decreasing function of distance along the longitudinal axis in a direction of flow through the nozzle.

20 Claims, 7 Drawing Sheets

NOZZLE FOR USE IN AN ULTRA-HIGH VELOCITY INJECTION DEVICE

RELATED APPLICATION

The present application claims the benefit of U.S. Application No. 62/018,809, entitled "Nozzle for Use in an Ultra-High Velocity Injection Device" and filed Jun. 30, 2014, which is hereby incorporated by reference in its entirety.

TECHNICAL FIELD

The present invention relates to injection devices, and more particularly to high velocity injection devices that do not require a needle.

BACKGROUND ART

Ultra-high velocity injection devices that do not require a needle are taught in the prior art, including in U.S. Pat. Nos. 7,833,189; 8,172,790; and 8,328,755. Each of these patents is hereby incorporated herein by reference in its entirety. U.S. Pat. No. 7,833,189 discloses that such devices can operate with exit velocities in excess of 100 meters per second. FIG. 6 of U.S. Pat. No. 8,172,790 shows exit velocities in the range of 100-200 meters per second for pressures above 5 MPa.

SUMMARY OF THE EMBODIMENTS

In a first embodiment of the invention there is provided a nozzle, for use in an injection device, that projects material at an ultra-high velocity. The nozzle includes an integrally formed body having an interior passageway from an input to an output, and the passageway has a longitudinal axis. The input of the nozzle is configured to interface with a cartridge. The output of the nozzle is configured to be placed proximate to a target. The passageway includes a taper, over a path length from an initial diameter at the input of the nozzle to a position along the passageway where the passageway first reaches a smallest diameter. The path length of the taper is at least about 0.5 mm in length. The taper defines a shape, in a plane that includes the longitudinal axis, that is a continuous and monotonically decreasing function of distance along the longitudinal axis in a direction of flow through the nozzle.

In a further related embodiment, the passageway has a cross-sectional area, and the taper of the passageway causes the cross-sectional area, as a function of distance along the longitudinal axis in the direction of flow, to decrease in a manner such that a first derivative of the function is negative, continuous, and monotonically increasing. The second derivative of this function is always negative along the path length.

Optionally, the path length is about 1.0 mm. Optionally, the shape of the taper has a non-zero second derivative over the path length. Also optionally, the shape of the taper may be approximately exponential. Also optionally, the first derivative of the shape of the taper has an approximately constant value over a portion of the taper.

The diameter at the output of the nozzle may be less than 300 μm. In another embodiment, the diameter at the output of the nozzle may be less than about 200 μm. In a further embodiment, the diameter at the output of the nozzle may be less than about 100 μm.

In various embodiments, the taper is shaped to provide a ratio of (1) radial velocity of material at the output of the nozzle to (2) axial velocity of material at the output of the nozzle, that is less than about 0.50. The taper may be governed by the equation $y=-15.8+1515.8e^{-0.0031372x}$. In other embodiments, the ratio is less than about 0.10. The taper may be governed by the equation $y=41.9+1458.1e^{-0.0003463x}$. In further related embodiments, the taper is shaped to provide, with suitable pressure of material at the input of the nozzle, an axial velocity of material at the output of the nozzle that is greater than about 100 m/s, and optionally, at least 200 m/s.

In another embodiment, there is provided a method of forming a micro beam of injectate. The method of this embodiment includes forcing the injectate through a passageway within a nozzle having a longitudinal axis and an exit orifice that is less than about 300 μm in diameter and located at a point where the passageway achieves its smallest diameter, to produce an axial flow of injectate at the exit orifice of at least about 100 m/s. The method further includes, while forcing the injectate through the passageway within the nozzle, constricting the cross-sectional area of the flow of the injectate in a smooth and continuous manner as the injectate moves toward the exit orifice, so as to produce the micro beam of injectate and to produce, at the exit orifice, flow of injectate characterized by a radial velocity component that is less than about 50% of an axial velocity component. The nozzle may have a taper governed by the equation $y=-15.8+1515.8e^{-0.0031372x}$. In a further related embodiment there is produced flow of injectate characterized by a radial velocity component that is less than about 10% of an axial velocity component. The nozzle may have a taper governed by the equation $41.9+1458.1e^{-0.003463x}$.

In another embodiment of the present invention, there is provided a nozzle for use in an ultra-high velocity injection device. The nozzle includes an integrally formed body having an interior passageway from an input to an output. The input is configured to interface with a cartridge. The output is configured to be placed proximate to a target. Further, the passageway includes a taper, over a path length from an initial diameter to a position along the passageway where the passageway first reaches a smallest diameter. Additionally, the path length of the taper is less than about 2.00 mm in length.

In some embodiments, the path length of the taper is less than 1.75 mm in length. The path length of the taper may be no more than 1.5 mm in length. Moreover, the taper defines a shape, in a plane that includes the longitudinal axis, that is monotonically decreasing and continuous along the path length. Furthermore, the taper may define a shape, in a plane that includes the longitudinal axis, that is approximately exponential or exponential.

BRIEF DESCRIPTION OF THE DRAWINGS

The foregoing features of embodiments will be more readily understood by reference to the following detailed description, taken with reference to the accompanying drawings, in which:

FIG. 1 is a representation of an exemplary nozzle, for an injection device that does not require a needle, of a type known in the prior art;

FIGS. 2 and 3 show embodiments of the present invention, wherein the input 105 interfaces with the cartridge 102, either by being integrally formed with the cartridge (as depicted in FIG. 2) or being configured to be coupled to the cartridge (as depicted in FIG. 3);

FIG. 4 is a representation of a nozzle having a two-stage taper, in accordance with an embodiment of the present invention, for an injection device that does not require a needle;

DETAILED DESCRIPTION OF SPECIFIC EMBODIMENTS

Figure 1:
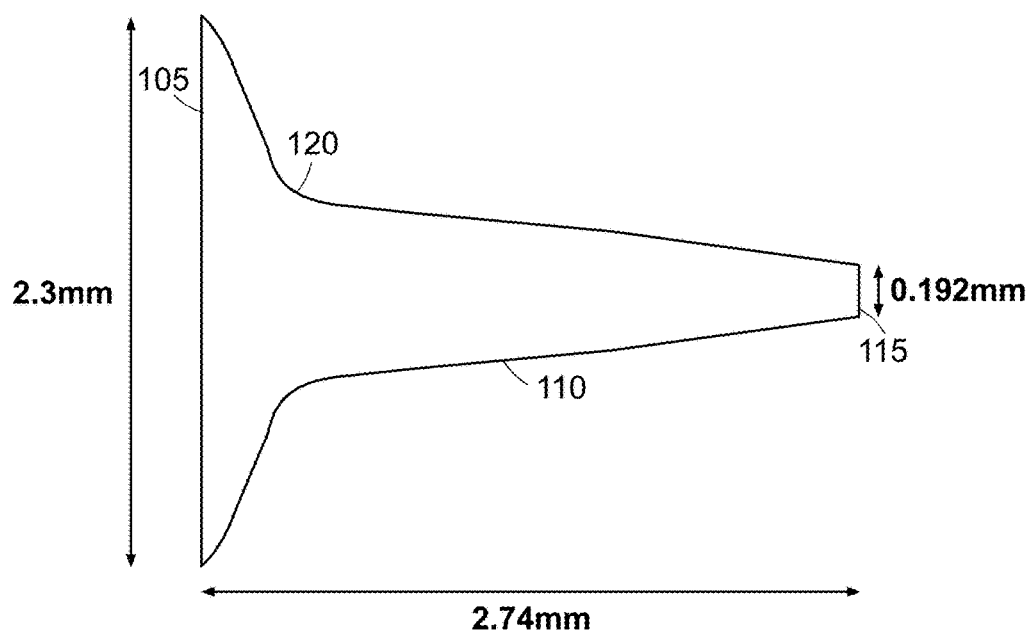
Figure 2:
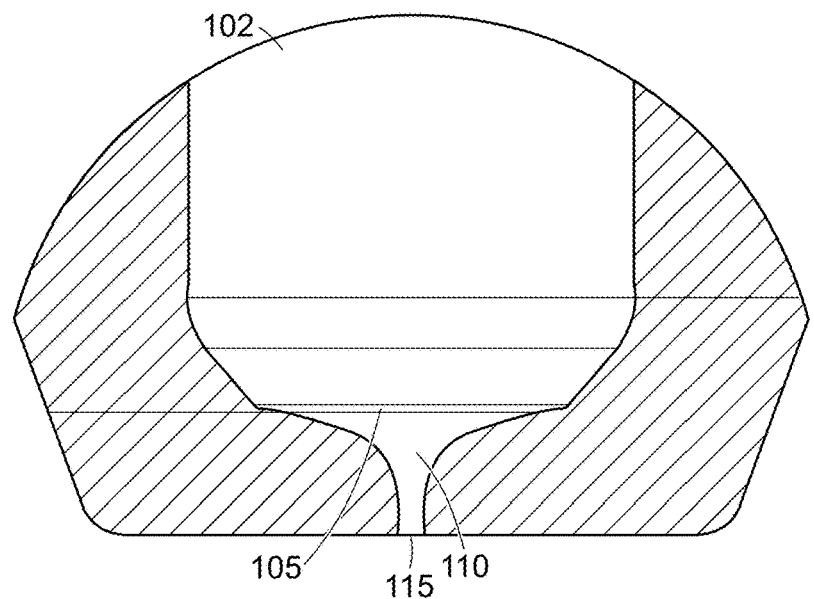
Figure 3:
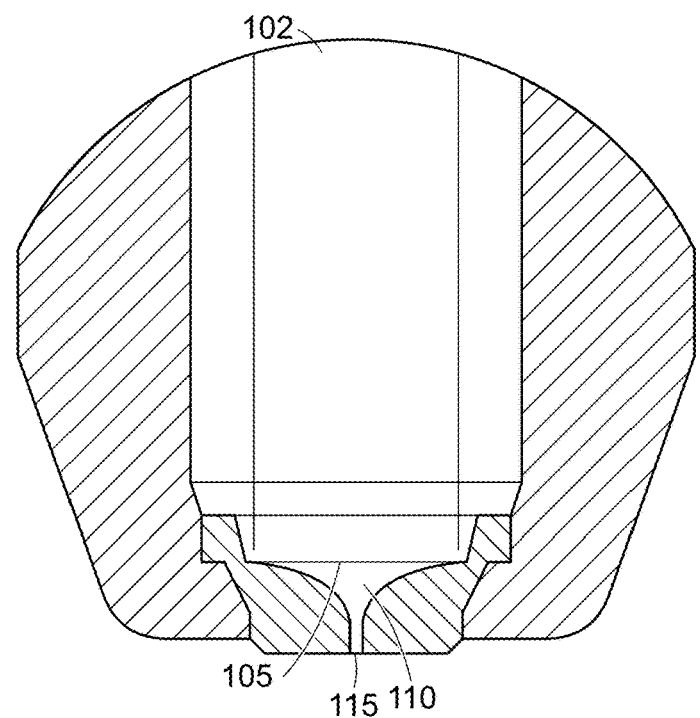
Figure 4:
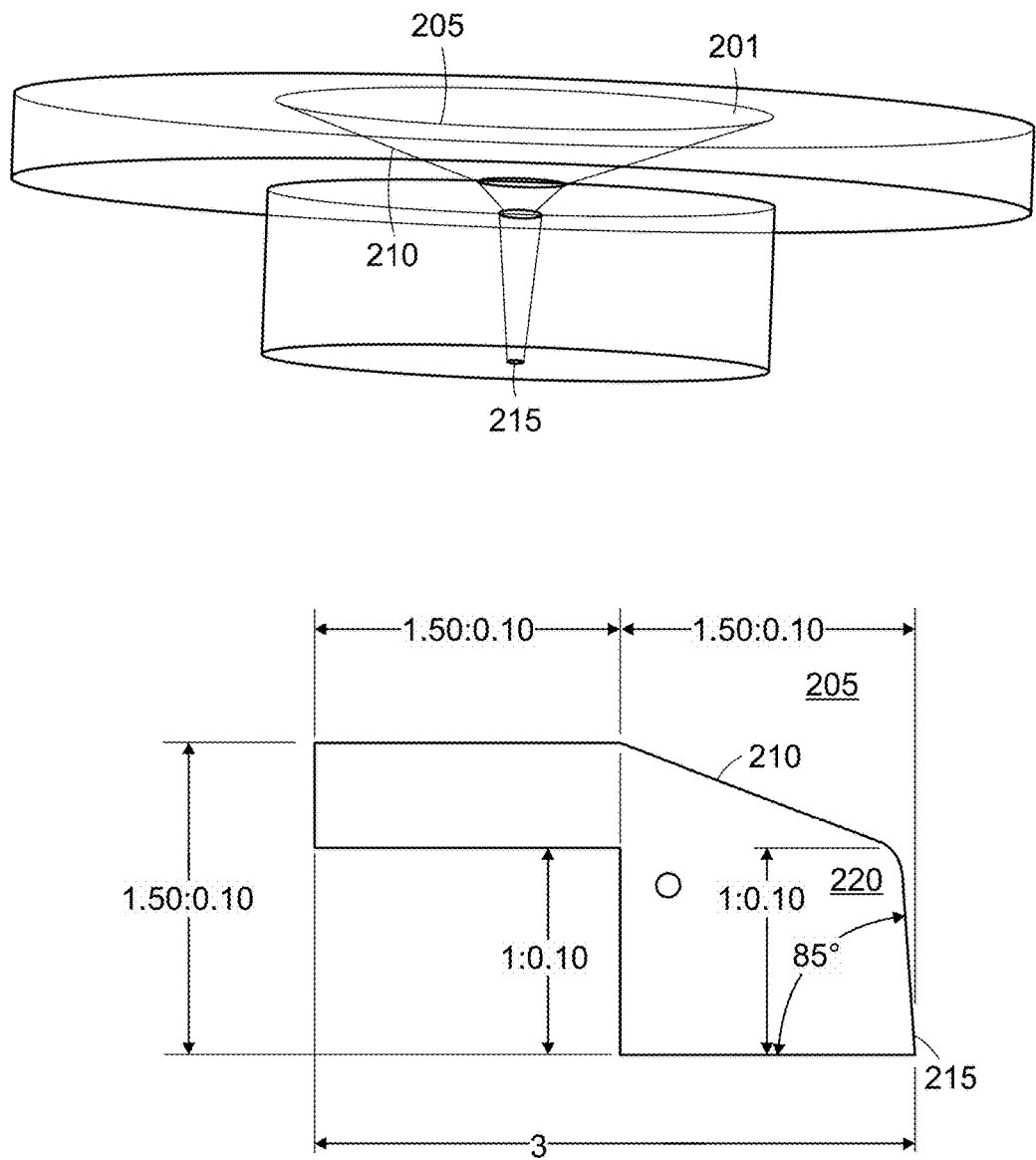

Definitions. As used in this description and the accompanying claims, the following terms shall have the meanings indicated, unless the context otherwise requires:

An "ultra-high velocity" injection device is an injection device having a nozzle from which the exit velocity of a material payload is at least 100 meters per second.

An "injection device" is a device for forming a payload of material into an ultra-high velocity micro beam and injecting it into a target, such as tissue of a human or another organism, or into an interior region of an inanimate object, having a surface capable of being penetrated by the micro beam.

A "cartridge" is a reservoir, removably insertable into an injection device, for holding material of which a quantity is deliverable by the injection device as a payload into the target subject.

A "micro beam" has a diameter, when leaving "an injection device" as defined herein, of 300 μm or less.

A fluid input of a nozzle is configured to "interface" with a cartridge when the input is integrally formed with the cartridge or when the input is coupled to the cartridge to enable flow of material from the cartridge to and through the nozzle.

A "passageway" within a nozzle has a longitudinal axis and an interior wall.

The "shape" of a passageway within a nozzle is the pair of opposed edges formed by the intersection of the interior wall of the passageway with a plane that contains the longitudinal axis of the passageway. In considering the "shape" as a function, it assumed, for purposes of this disclosure, to always have a positive value. In various embodiments described herein, the passageway has radial symmetry about the longitudinal axis.

A "taper" of a passageway within a nozzle is a shape (as defined) of the portion in the passageway that provides a decrease in diameter of the passageway along the longitudinal axis so that the slope of the shape changes along the length of the longitudinal axis. In some embodiments, the decrease is smooth throughout the length of the passageway, and in other embodiments, the decrease occurs in stages.

A taper of a passageway is "approximately exponential" if the shape (as defined) of the passageway is defined by a function that is monotonically decreasing and continuous; this term includes hyperbolic, parabolic, quadratic, and Gaussian functions, as well as polynomial expressions, and a linear combination of Hermite polynomials.

The "path length" of a taper of a passageway in a nozzle is the length along the longitudinal axis of the passageway from an initial diameter of the passageway at a beginning of the taper to a position on the longitudinal axis where the passageway first reaches a smallest diameter. Often the position along the longitudinal axis where the passageway first reaches the smallest diameter is at the output of the nozzle. If, however, the nozzle includes a flare at the output or a tunnel of constant diameter near the output, the position where the passageway first reaches the smallest diameter will be somewhat displaced, from the output of the nozzle, in a direction toward the input.

In numerous applications, nozzles in accordance with the present invention are used in injection devices, among other things, to deliver therapeutic materials (i.e., injectates) into patients' bodies, although a wide variety of other payloads may be delivered to a wide variety of targets. In various embodiments, the payload may include one or more types of materials. Further, the payload may encompass a single phase (e.g., all liquid or all solid or all gas) or a plurality of phases (e.g., a combination of a solid phase of at least one composition and a liquid phase of at least one other composition). For example, the payload may include a liquid phase that includes a solvent system of one or more solvents in which one or more solutes are dissolved. Alternatively or in addition, the liquid phase may be a dispersion medium in which finely divided particles of one or more compositions in the solid phase are dispersed so as to form a colloid or a suspension. Further, payloads with materials in a plurality of phases may assume any one of a range of forms, such as aerosols, foams, emulsions, suspensions, colloids, sols, or gels. In many embodiments, the payload may be constituted by any of a wide range of single compositions or combinations of compositions. A principal constraint on the nature of the payload, beyond requirements of stability as a function of time and temperature and other environmental considerations, including those applicable to the payload when it is being administered, is that the payload should exhibit a viscosity within the range of about $8.90*10^{-4}$ Pa·s (0.89 cP) up to about 1000 Pa·s (1,000,000 cP).

Further, nozzles in accordance with the present invention are used in injection devices to deliver payloads to a wide variety of targets in addition to human subjects. The targets may also be other living organisms, including animals, plants, fruits, and seeds, as well as inanimate objects.

When an injection device to which embodiments of the present invention are applicable is used to deliver a payload to a patient, after a user loads a cartridge of a therapeutic material into a device, the user positions the device near a patient's skin. In response to a user control (e.g., pressing a button), an actuator propels the payload out of the cartridge and through a nozzle to form a micro beam of fluid. The beam exits the nozzle at a sufficiently high velocity to penetrate the patient's skin and deliver the payload to a particular depth in the patient's tissue.

The configuration of the nozzle, which may be integrally formed with the cartridge or formed as a distinct component of the injection device that may be coupled to the cartridge, impacts how effectively the therapeutic material is delivered into a patient's body. In particular, the nozzle configuration determines the manner in which the payload is projected. If the nozzle disperses the payload over a larger surface area, the patient may experience greater discomfort or pain during treatment, and the payload would provide to the skin reduced pressure per unit area and consequently have a more difficult time of penetrating the skin. Further, if the configuration promotes turbulence as the payload passes through the length of the nozzle, particularly the path length of the taper, the turbulence may damage the therapeutic material, diminish the velocity of the beam, or otherwise detract from the quality of the beam. Additionally, the configuration influences the shearing that the payload experiences from the inner walls of the nozzle as it is expelled from the cartridge. If a configuration induces higher shearing, the shearing may cause molecular damage of the payload. Thus, a configuration that minimizes this damage is desirable.

The nozzles described herein deliver ultra-high velocity beams of therapeutic materials, or other payloads, with lower dispersion, lower turbulence, and lower pressure within the nozzle than those of the prior art. When used with an injection device, an exemplary nozzle can project a material at about 200 m/s, a velocity effective for tissue penetration. Further, some embodiments of the nozzle project beams of material that maintain the same diameter for a distance of at least 18 mm. Assuming that the nozzle is placed in contact with the skin, the low dispersion is beneficial in maintaining the geometry of the micro beam as it penetrates the skin.

To highlight the differences between the configurations of this disclosure's nozzles over the prior art, an exemplary prior art nozzle 101 for an injection device that does not require a needle is depicted in FIG. 1. The nozzle 101 includes an input 105 that is about 230 μm in diameter, a passageway 110 that is about 2.74 mm long, and an output 115 that is about 192 μm in diameter. Although diameters of prior art inputs and outputs may vary, in many embodiments, the path lengths of the tapers within the passageways are at least about 2.00 mm in length.

The relatively large path length of the taper in comparison to the diameter of the output may be attributed to the belief in the prior art that such a length would be of assistance in concentrating the beam of material leaving the output of the nozzle. Surprisingly, our analysis has shown that a path length of the magnitude of this example in the prior art is less than optimal in concentrating the beam of material and in fact introduces turbulence.

In this embodiment of the prior art, the slope of the passageway 110 changes abruptly at the crook 120. At in the region surrounding crook 120, the slope of the passageway taper first increases, then it decreases. Our analysis has shown that the crook 120 in the passageway 110 of the nozzle 101 introduces turbulence. When the payload flows through the passageway 110, as the payload passes over the crook 120, the sudden change in slope perturbs the payload and appears to be a source of turbulence. Further, we have found that that excessive length of the taper in the passageway in the nozzle 101 causes a dispersive beam (i.e. a beam whose diameter starts increasing immediately at the nozzle exit) and increases the possibility of turbulence near the output.

In contrast, nozzles in accordance with embodiments of the invention described herein are configured to expel a micro beam of payload that substantially maintains its original diameter at the nozzle output over a considerable distance. For some exemplary embodiments of the invention, we have observed that over a distance of 18 mm away from the nozzle exit, there seems to be no appreciable difference in the micro beam diameter. In other exemplary embodiments, we have observed that at a distance of about 18 mm away from the nozzle exit, the micro beam diameter has increased by less than a factor of 2.0.

Our studies have shown us that we can achieve these results, for nozzles handling ultra-high velocity flow and providing a micro beam of payload, when the passageway has a taper geometry that decreases monotonically and continuously, and, in further embodiments, the taper has a path length no greater than about 2.00 mm. Moreover, when the taper geometry decreases monotonically and continuously and further is convex when viewed in a direction of flow through the nozzle, the nozzle achieves the desired results even when its path length is as little as about 0.5 mm. In the other direction, namely with longer path lengths, with this taper geometry, a nozzle may continue to provide advantages over the prior art even when its path length is greater than 2.00 mm.

Because the payload does not encounter sudden changes in slope of the passageway, the configuration of the nozzle in these embodiments of the present invention generates a reduced amount of turbulence in the payload and promotes formation of a beam with low dispersion. Our analysis indicates that an exemplary velocity component of the payload in the passageway near the output of the nozzle that is perpendicular to the length of the nozzle 101 (i.e., the radial velocity of the material) may be as little as about 2-10% of the velocity component of the payload extending along the length of nozzle (i.e., the axial velocity of the material), as is the case for the nozzle embodiment of FIG. 5, which produces a fluid micro-beam shown in FIG. 8. In particular, for the embodiment of FIG. 5, the radial velocity is about 2-3% of the axial velocity. In various embodiments, the radial velocity is less than about 50% of the axial velocity of the projected material, as is the case for the nozzle embodiment of FIG. 6, which produces a fluid micro-beam shown in FIG. 9. In particular, for the embodiment of FIG. 6, the radial velocity is about 30% of the axial velocity. Put another way, in some embodiments, the ratio of the radial velocity to the axial velocity is less than about 0.50, and in various embodiments, the ratio is less than about 0.10 or as little as less than about 0.02. For the embodiments of FIGS. 5 and 6, the ratios are about 0.02-0.03 and 0.30, respectively. Given this range of effective ratios, the extent to which the micro beams projected from such nozzles maintain their diameters will vary. The micro beams may increase their diameter by about 2.0×, at a distance of about 18.0 mm from the output of the nozzle, as is the case for the nozzle embodiment of FIG. 6, which produces a fluid micro-beam shown in FIG. 9. In some embodiments, the micro beams maintain their initial exit diameters at this distance, as well. In some embodiments of the present invention, the taper of the passageway benefits from a geometry that decreases monotonically and continuously. In further related embodiments, the taper geometry may be defined by an exponential or approximately exponential curve. By "approximately exponential" we mean that the taper is defined by a function that is monotonically decreasing and continuous; this term includes hyperbolic, parabolic, quadratic, and Gaussian functions, as well as polynomial expressions and a linear combination of Hermite polynomials. However, other mathematical expressions may also be used.

In some embodiments, although the taper geometry decreases monotonically, the decrease may occur in stages. For example, a first portion of the taper geometry, beginning from the input of the nozzle, may be defined by an exponential or approximately exponential curve. The remaining portion of the taper geometry may decrease linearly, i.e., its first derivative may remain a constant value and its second derivative may be zero (0) over the remaining path length. Alternatively, the beginning portion of the taper geometry may decrease linearly, and the ending portion of the taper geometry may be defined by the exponential or approximately exponential curve.

In various embodiments, the taper geometry may alternate between portions that decrease linearly and portions defined by one or more exponential or approximately exponential curves. For example, in accordance with one embodiment, the beginning portion of the taper geometry decreases linearly, the middle portion is defined by an exponential or approximately exponential curve, and the ending portion decreases linearly. Alternatively, the beginning and ending portions can be defined by one or more exponential or approximately exponential curves, and the middle portion decreases linearly. In any of these embodiments, the linearly decreasing portions can exhibit the same or different slope, and the curved portions can be defined by the same or different exponential or approximately exponential curves.

In some embodiments, the taper geometry exhibits a non-zero second derivative. In this manner, the shape defined by the taper is convex, as when viewed in the direction of flow through the nozzle. Further, our analysis has shown that nozzles according to embodiments of the present invention expel payloads with less turbulence than do nozzles in the prior art. At least one factor that accounts for this diminished turbulence is the shorter path length. Nevertheless, a minimum path length is still required to form a micro beam with the desired dispersion and/or velocity. Our studies that shown that nozzles with path lengths less than about 0.50 mm form micro beams with dispersion comparable to the prior art's, or micro beams with velocities that are not ultra-high. Therefore, the nozzles disclosed herein have path lengths that are at least about 0.50 mm. Since a path length of less than about 0.5 mm leads to dispersion of the micro beam when it emerges from the nozzle; the minimum path length of an embodiment of a nozzle in accordance with the present invention is that which does not produce unacceptable dispersion of the micro beam. For example, a nozzle may be about 0.50, 1.00, or 1.50 mm in length, although other lengths may be used.

In various embodiments, the taper of the passageway causes the cross-sectional area of the passageway to decrease as a function of distance along the longitudinal axis in the direction of flow. The first derivative of the function is negative, continuous, and monotonically increasing, and the second derivative of this function is always positive along the path length.

The nozzles described herein may have inputs that are about 3.0 mm in diameter, although other sizes of diameters may be used. Further, the outputs may be between about 50 μm to about 300 μm in diameter. In some embodiments, the output is about 100 μm in diameter such that the nozzle promotes a beam that maintains a diameter of about 100 μm. However, other sizes of diameters may also be used.

FIGS. 2 and 3 show embodiments of the present invention, wherein the input 105 interfaces with the cartridge 102, either by being integrally formed with the cartridge (as depicted in FIG. 2) or being configured to be coupled to the cartridge (as depicted in FIG. 3). Thus, the nozzle 101 receives a payload from the cartridge 102 via the input 105, and the passageway 110 guides the payloads to be expelled through the output 115. As we have discussed, the configuration of the passageway 110 affects how the payloads are projected from the output 115.

FIGS. 4-6 are exemplary representations of nozzles according to various embodiments of the present invention. FIG. 4 is a representation of a nozzle 201 having a two-stage taper 210, for an injection device that does not require a needle. The nozzle 201 has an input 205 that is about 3.0 mm in diameter, a passageway 210 that is about 1.5 mm in length, and an output 215 that is about 100 μm in diameter. The passageway 210 has two stages. The first stage extends for about the first 0.5 mm of the nozzle. During this first stage, the slope of the passageway 210 exhibits a first value. At a shoulder 220 in the passageway 210, the slope of the passageway 210 transitions into a second value. Unlike the prior art, whose magnitude (i.e., absolute value) of slope of the passageway 110 increases and then decreases, the magnitude of the slope of this embodiment of the nozzle 201 decreases, albeit quickly. Thus, the nozzle 201 is capable of projecting, at ultra-high velocity, a beam of a payload that also that maintains its particular diameter.

FIG. 5 is a representation of a nozzle 301 having a single stage taper, in accordance with an embodiment of the present invention, for an injection device that does not require a needle. The nozzle 301 has an input 305 of about 3 mm in diameter, a passageway 310 about 1.5 mm in length, and an output 315 of about 100 μm in diameter. The geometry of the passageway 310 is continuous and monotonically decreasing. In this embodiment, the configuration of the passageway 310 may be modeled according to the equation $$y=41.9+1458.1e^{-0.003463x}$$

where y is the distance (in micrometers) between the passageway 310 and the center axis of the nozzle 301 and x is the position along the length of the passageway 310. Because the taper geometry is continuous and monotonically decreasing and the magnitude of the slope decreases over the passageway 310, the nozzle 301 is capable of projecting, at ultra-high velocity, a beam of a payload that also maintains its particular diameter. Further, when a payload flows through the passageway 310, the pressure needed to expel the payload is about 18 MPa, and the payload experiences a maximal shear stress of about 80 kPa at the nozzle wall near the nozzle exit.

Likewise, FIG. 6 is another representation of a nozzle 401 having a single stage taper, in accordance with an embodiment of the present invention, for an injection device that does not require a needle. The nozzle 401 has an input 405 of about 3 mm in diameter, a passageway 410 about 1.0 mm in length, and an output 415 of about 100 μm in diameter. The geometry of the passageway 410 is continuous and monotonically decreasing. In this embodiment, the configuration of the passageway 410 may be modeled according to the equation $$y=-15.8+1515.8e^{-0.0031372x}$$

where y is the distance (in micrometers) between the passageway 410 and the center axis of the nozzle 401 and x is the position along the length of the passageway 410. Because the taper is continuous and monotonically decreasing and the magnitude of the slope decreases over the passageway 401, the nozzle 401 is capable of projecting, at ultra-high velocity, a beam of a payload that also that maintains its particular diameter. Further, when a payload flows through the passageway 310, the pressure needed to expel the payload is about 17.6 MPa, and the payload experiences a maximal shear stress of about 140 kPa at the nozzle wall near the nozzle exit.

Figure 6:
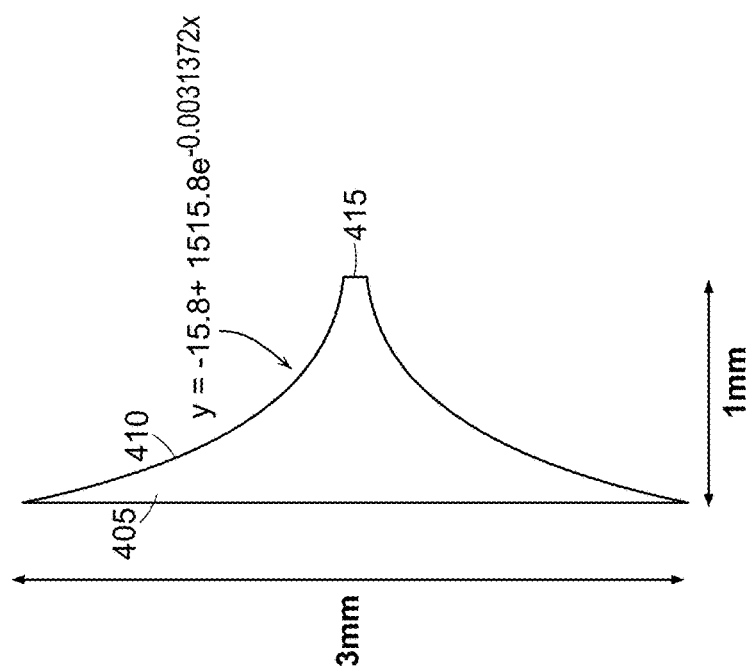
FIG. 6 is a representation of a nozzle having a single stage taper, in accordance with another embodiment of the present invention, for an injection device that does not require a needle.
Figure 5:
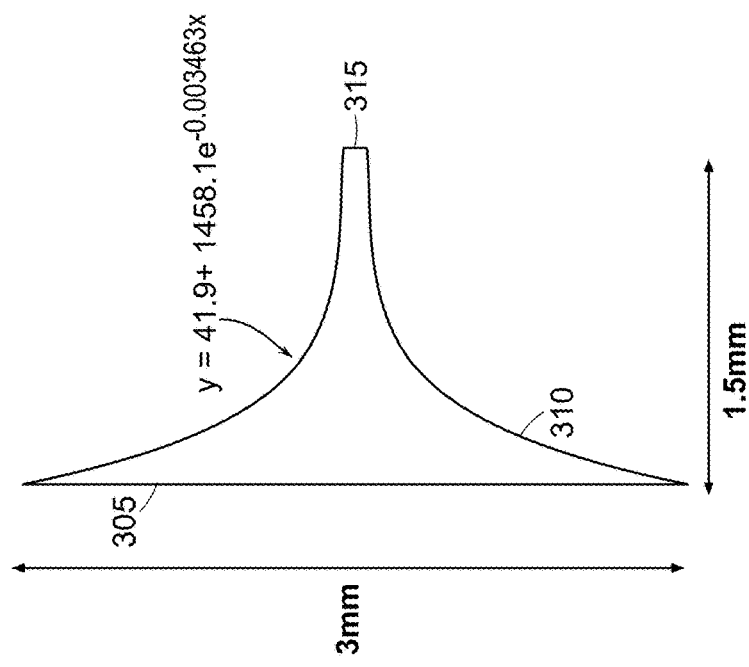
FIG. 5 is a representation of a nozzle having a single stage taper, in accordance with an embodiment of the present invention, for an injection device that does not require a needle.
Figure 7:
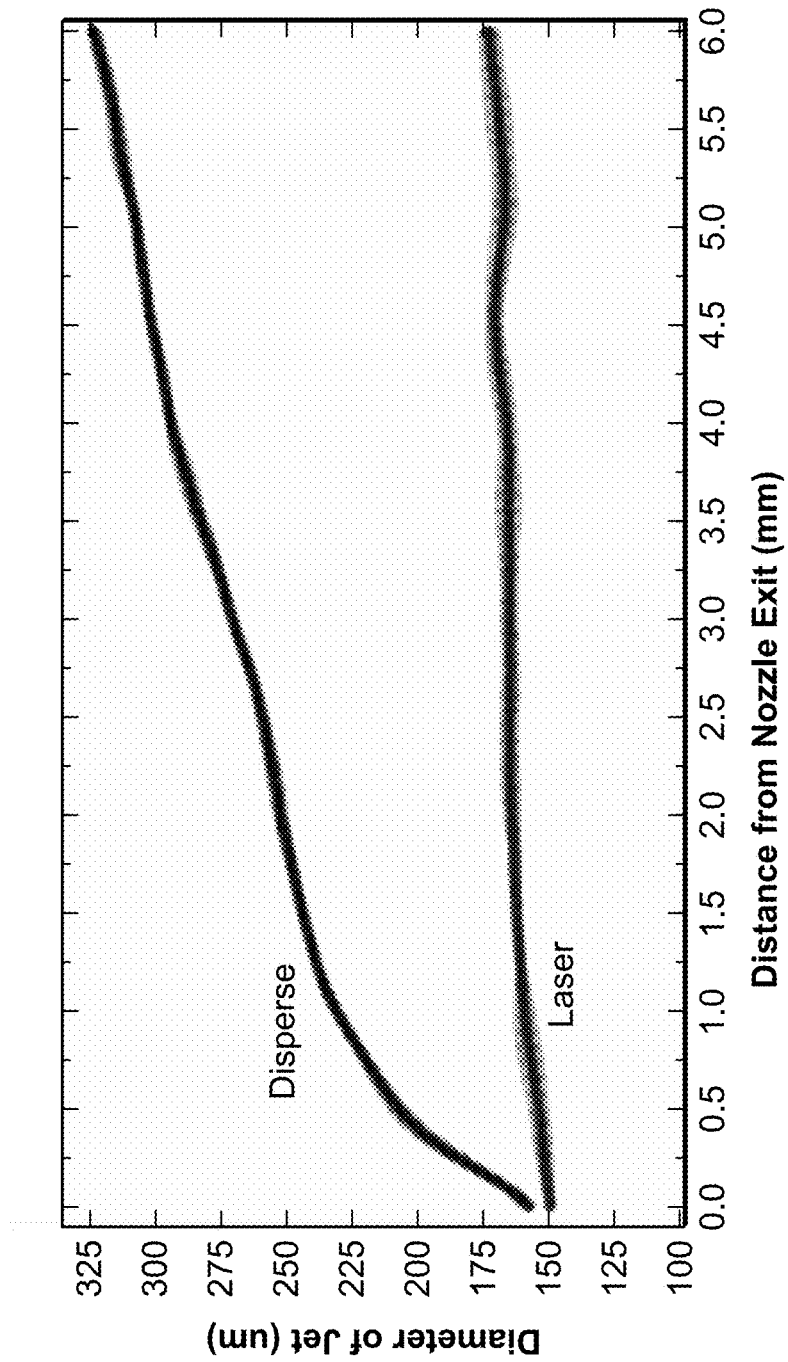
FIG. 7 is a graph comparing the measured diameter of a micro beam projected from the embodiment of the invention shown in FIG. 5 (described as the "Laser") and the measured diameter of a micro beam projected from the embodiment of the invention shown in FIG. 6 (described as the "Disperse")
Figure 8:
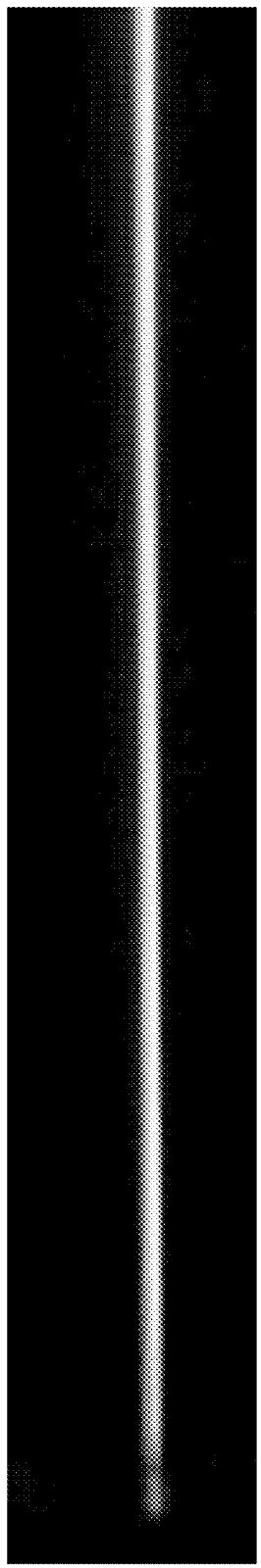
FIG. 8 is a photograph showing dispersion of a micro beam projected from the embodiment of the invention shown in FIG. 5.
Figure 9:
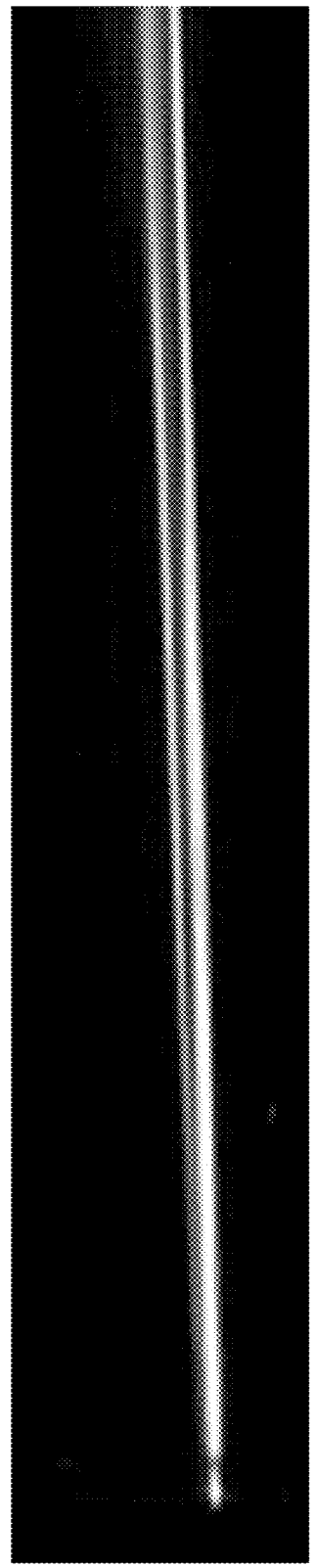
FIG. 9 is a photograph showing the dispersion of a micro beam projected from the embodiment of the invention shown in FIG. 6.
Figure 10:
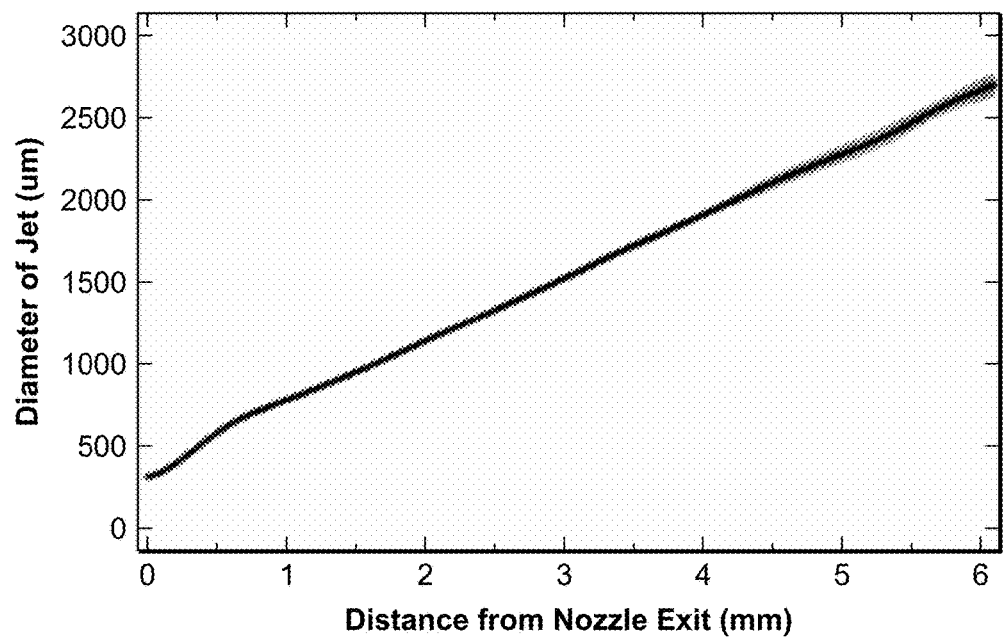
FIG. 10 is a graph depicting the measured diameter of a micro beam projected from a prior art nozzle, such as the nozzle depicted in FIG. 1.
Figure 11:
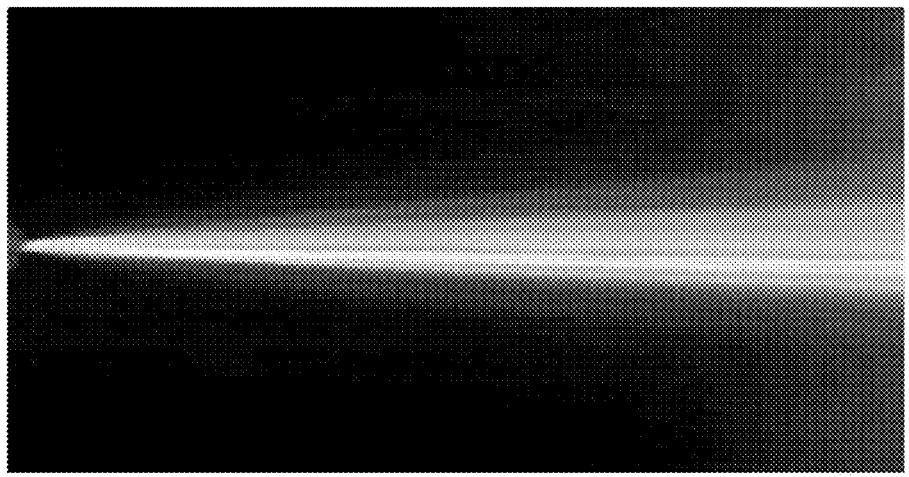
FIG. 11 is a photograph showing the dispersion of a micro beam projected from the prior art nozzle of FIG. 10.

FIG. 7 is a graph plotting, as a function of distance from the nozzle exit, the diameter of a micro beam projected from the embodiment of the invention shown in FIG. 5 as well as the diameter of a micro beam projected from the embodiment of the invention shown in FIG. 6. With respect to the former, this graph contemplates nozzles whose outputs are 150 μm in diameter, and FIG. 8 depicts a photograph showing the dispersion of micro beams projected from such nozzles. As this graph further demonstrates, when a payload of material is projected through a nozzle designed to be dispersive, such the nozzle depicted in FIG. 6, at a distance of merely 6.0 mm from the nozzle output, the diameter of the micro beam has already expanded to almost 325 μm. In this manner, the nozzle geometry may be designed to produce micro beams of different sized diameters.

This greater dispersion of prior art nozzles is illustrated in FIGS. 10 and 11. FIG. 10 is a graph plotting, as a function of distance from the nozzle exit, the diameter of a micro beam projected from a prior art nozzle, such as the nozzle depicted in FIG. 1. FIG. 11 is a photograph showing the dispersion of a micro beam projected from the prior art nozzle of FIG. 10. As the graph in FIG. 10 demonstrates, the diameter of a micro beam projected from a prior art nozzle may expand to more than 2500 μm at a distance of merely 6.0 mm from the output. In this manner, the micro beam exhibits a diameter more than an order of magnitude larger than the micro beam projected by the embodiments depicted in FIGS. 5 and 9. Thus, the advantages of the micro beams formed by embodiments of the invention become even more apparent.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A nozzle for use in an injection device, the nozzle projecting material at an ultra-high velocity, the nozzle comprising an integrally formed body having an interior passageway from an input to an output, the passageway having a longitudinal axis, wherein (i) the input of the nozzle is configured to interface with a cartridge, (ii) the output of the nozzle is configured to be placed proximate to a target, and (iii) the passageway includes a taper, over a path length from an initial diameter at the input of the nozzle to a position along the longitudinal axis where the passageway first reaches a smallest diameter, (iv) the path length of the taper is at least about 0.5 mm in length, and (v) the taper of the passageway defines a shape, in a plane that includes the longitudinal axis, that is a continuous and monotonically decreasing function of distance along the longitudinal axis in a direction of flow through the nozzle, wherein a rate of change of a cross-sectional distance, in μm, of the passageway from the longitudinal axis is exponential with an exponential term in the form of $e^{-\alpha x}$, where x is a displacement along the longitudinal axis and α is in a range of 0.0031372 $\mu m^{-1}$ to 0.003463 $\mu m^{-1}$.

2. A nozzle according to claim 1, wherein the passageway has a cross-sectional area, and the taper of the passageway causes the cross-sectional area, as a function of distance along the longitudinal axis in the direction of flow, to decrease in a manner such that a first derivative of the function is negative, continuous, and monotonically increasing, and wherein a second derivative of this function is always positive along the path length.

3. A nozzle according to claim 1, wherein the path length is about 1.0 mm.

4. A nozzle according to claim 1, wherein the shape of the taper has a non-zero second derivative over the path length.

5. A nozzle according to claim 1, wherein the shape of the taper is approximately exponential.

6. A nozzle according to claim 1, wherein a first derivative of the shape of the taper has an approximately constant value over a portion of the taper.

7. A nozzle according to claim 1, wherein a diameter at the output of the nozzle is less than 300 μm.

8. A nozzle according to claim 1, wherein a diameter at the output of the nozzle is less than about 200 μm.

9. A nozzle according to claim 1, wherein a diameter at the output of the nozzle is less than about 100 μm.

10. A nozzle according to claim 1, wherein the taper is shaped to provide a ratio of (1) radial velocity of material at the output of the nozzle to (2) axial velocity of material at the output of the nozzle, that is less than about 0.50.

11. A nozzle according to claim 10, wherein the taper is governed by the equation $y=-15.8+1515.8e^{-0.0031372x}$.

12. A nozzle according to claim 1, wherein the taper is shaped to provide a ratio of (1) radial velocity of material at the output of the nozzle to (2) axial velocity of material at the output of the nozzle, is less than about 0.10.

13. A nozzle according to claim 12, wherein the taper is governed by the equation $y=41.9+1458.1e^{-0.003463x}$.

14. A nozzle according to claim 1, wherein the taper is shaped to provide, with suitable pressure of material at the input of the nozzle, an axial velocity of material at the output of the nozzle that is greater than about 100 m/s.

15. A nozzle according to claim 1, wherein the taper is shaped to provide, with suitable pressure of material at the input of the nozzle, an axial velocity of material at the output of the nozzle that is at least 200 m/s.

16. A nozzle for use in an ultra-high velocity injection device, the nozzle comprising an integrally formed body having an interior passageway from an input to an output, wherein (i) the input is configured to interface with a cartridge, (ii) the output is configured to be placed proximate to a target, (iii) the passageway includes a taper, over a path length from an initial diameter to a position along the passageway where the passageway first reaches a smallest diameter, and (iv) the path length of the taper is less than 2.00 mm in length, wherein a rate of change of a cross-sectional distance, in μm, of the passageway from a longitudinal axis of the passageway is exponential with an exponential term in the form of $e^{-\alpha x}$, where x is a displacement along the longitudinal axis and α is in a range of 0.0031372 $\mu m^{-1}$ to 0.003463 $\mu m^{-1}$.

17. A nozzle according to claim 16, wherein the path length of the taper is less than 1.75 mm in length.

18. A nozzle according to claim 16, wherein the path length of the taper is no more than 1.50 mm in length.

19. A nozzle according to claim 16, wherein the taper defines a shape, in a plane that includes the longitudinal axis, that is monotonically decreasing and continuous along the path length.

20. A nozzle for use in an ultra-high velocity injection device, the nozzle comprising:

an integrally formed body having an input and an output;
a passageway from the input to the output, wherein the input is configured to interface with a cartridge and the output is configured to be placed proximate to a target;
a taper to the passageway over a path length less than 2.00 mm in length from an initial diameter to a position proximal to the output where the interior first reaches a smallest diameter, wherein a rate of change of a cross-section distance from a longitudinal axis of the passageway from the initial diameter to the position proximal to the output is exponential with a value, in microns, as a function of distance from displacement along the longitudinal axis between $41.9+1458.1e^{-0.003463x}$ and $-15.8+1515.8e^{-0.0031372x}$.

* * * * *